United States Patent [19]

Imran

[11] Patent Number: 4,705,043
[45] Date of Patent: Nov. 10, 1987

[54] ELECTROPHYSIOLOGY STUDY SYSTEM USING IMPLANTABLE CARDIOVERTER/PACER

[75] Inventor: Mir Imran, Gibsonia, Pa.

[73] Assignee: Mieczslaw Mirowski, Owings Mills, Md.

[21] Appl. No.: 751,964

[22] Filed: Jul. 5, 1985

[51] Int. Cl.$^4$ .............................................. A61N 1/36
[52] U.S. Cl. ............................ 128/419 PG; 128/697; 128/903
[58] Field of Search .................. 128/419 PG, 419 PT, 128/697, 903

[56] References Cited

U.S. PATENT DOCUMENTS

| | | | |
|---|---|---|---|
| 3,433,228 | 3/1969 | Keller, Jr. | 128/419 PG |
| 3,683,934 | 8/1972 | Bukowiecki et al. | 128/419 PG |
| 3,717,153 | 2/1973 | Bowers | 128/419 PG |
| 4,041,954 | 8/1977 | Ohara | 128/697 |
| 4,187,854 | 2/1980 | Hepp. et al. | 128/419 PG |
| 4,223,679 | 9/1980 | Schulman et al. | 128/419 PT |
| 4,232,679 | 11/1980 | Schulman | 128/419 PG |
| 4,335,727 | 6/1982 | McPherson | 128/419 PG |
| 4,407,288 | 10/1983 | Langer et al. | 128/419 PG |

OTHER PUBLICATIONS

Kazutaka Aonuma, John J. Rozanski, S. Serge Barold, Paul L. Dewitt, Arthur J. Gosselin and John W. Liser PACE Magazine, vol. 8, Mar.-Apr., 1985, pp. 215-224, "Externally Activated Antitachycardia Pacemaker with Noninvasive Electrophysiologic Re-testing Capability".

Primary Examiner—William E. Kamm
Attorney, Agent, or Firm—Fleit, Jacobson, Cohn & Price

[57] ABSTRACT

An electrophysiology (EP) study system using an implantable cardioverter/pace. The system includes an implantable unit having a conventional programmable pace capable of operation in at least the VVT mode. The implantable unit transmits ECG data, in real time, externally of the patient and receives pacing pulse signals from an external unit. The pacing pulse signals are detected and provided to a trigger input of the pacer placed in the VVT mode. Simultaneously, the ECG data is transmitted to the external unit. The external unit detects the ECG data and provides the data to a conventional programmable electrical stimulator. The stimulator pacing pulse output is transmitted to the internal unit and provided to the trigger input of the pacer.

10 Claims, 2 Drawing Figures

ELECTROPHYSIOLOGY STUDY SYSTEM USING IMPLANTABLE CARDIOVERTER/PACER

BACKGROUND OF THE INVENTION

This invention relates to a system for conducting electrophysiology ("EP") studies on a patient's heart using an implantable cardioverter/pacer. The implantable device, after being placed in an "EP study" mode, receives pacing trigger pulses that are transmitted to the system by an external transmitter/receiver unit. These trigger pulses are provided as an input to the implantable device to control the cardiac pacing pulses applied to the heart of the patient. Electrocardiogram ("ECG") signals are simultaneously transmitted from the implantable system, in real time, to the external unit.

EP studies of the heart are frequently required to test the heart's reaction to a variety of treatments. For example, such EP studies typically require the delivery of various cardioverting and pacing pulses to the heart to determine the response of the heart to such pulses. Such information is desirable prior to surgical implants of pacers, cardioverters or defibrillators.

For example, as part of the implant procedure for automatic cardioverter/defibrillators, it is necessary to determine the energy level threshold needed to cardiovert or defibrillate the patient's heart. These patient thresholds are customarily evaluated prior to implant through implanted electrodes that extend from the heart of the patient. The procedure generally involves, first, the implantation of the cardioverter/defibrillator electrodes that are believed to be most suitable for the particular patient, second, exercising the patient by inducing an arrhythmia that is most likely to occur within the particular patient, and, third, attempting to cardiovert or defibrillate the patient to establish the desired energy level for the implanted device. The various arrhythmias can be induced by electrically stimulating the heart through the implanted electrodes by an external device. Pacing pulses are typically used to stimulate the heart from normalcy to an arrhythmia condition. Once the patient involved in the EP study is experiencing the desired fatal arrhythmia, the external unit is fired through the implanted electrodes in an attempt to convert the arrhythmia. This procedure is repeated until the physician learns which arrhythmias may reoccur in the particular patient and the threshold energy at which the patient can be brought out of the arrhythmia and return to normalcy.

One technique for conducting EP studies is through the use of an external programmable electrical stimulator which is connected with the heart tissue by wires extending through the skin of the patient to implanted electrodes. Such programmable electrical stimulator systems receive ECG information of the heart, through conventional ECG skin electrodes attached to the skin of the patient, and provide pacing pulses to the implanted electrodes for delivery to the heart. These conventional programmable stimulators may deliver pacing pulses in various standard pacing modes. The operator of the unit can select the particular pacing pulse sequence by manipulation of various dials or switches on the stimulator. A disadvantage of this technique is that an invasive procedure is necessary to implant the pacing electrodes each time an EP study is required.

EP studies are frequently desirable for persons who have already received an implantable pacer or cardioverter. Sophisticated pacers often include a non-invasive communication link whereby signals may be transmitted from outside the body to direct the pacer to emit stimulating pulses of a predetermined type or sequence which have been pre-programmed within the implantable pacer. While such systems may have utility in conducting EP studies, and overcome the disadvantage of requiring further invasive electrode implant procedures, nevertheless the EP study is limited to the particular pacing pulse sequence that had been programmed into the unit. Moreover, ECG skin electrodes, or even implanted electrodes, are still required to detect the ECG information, in real time, during the EP study.

U.S. Pat. No. 4,187,854 discloses an implantable pacing unit that is capable of both transmitting ECG information, without wires, to an external unit, and of receiving electromagnetic energy from the external unit to power the implant and to deliver pacing pulses. A disadvantage of this system is that the sole energizing source for the pacing pulses resides in the external unit. Thus, the implanted unit cannot operate independently as a pacer without the external unit. While such a system may be useful in conducting an EP study, it would appear unable to also perform as an implantable pacer having an independent implantable power source, thus lacking the versatility of the present invention.

SUMMARY OF THE INVENTION

The present invention permits EP studies to be conducted through the use of conventional programmable implantable pacer technology. The cardioverter/pacer, which may be set in a variety of conventional pacing modes (e.g., VOO, VVI, VVT and Burst), is connected with implantable electrodes (such as bipolar electrodes) attached to the ventricle of a patient's heart. Pacing pulses are delivered to the heart, through the implantable electrodes, in accordance with the pacing mode selected. The electrodes also receive the ECG signals of the heart, which signals pass through conditioning circuits that detect the heart R-waves. The R-waves may be applied to the trigger input of the pacer for synchronizing the pacing pulses with the R-waves when the pacer is in the VVT mode. Mode changes may be effectuated through the use of an implantable receiver and control logic system which decodes mode change information transmitted from an external unit.

When an EP study is desired, the implantable system detects EP mode signal information and places the pacer in a VVT mode, such that pacing pulses would ordinarily be applied to the heart of a patient in synchronism with the detected R-wave. A logical switch within the unit, however, uncouples the implantable electrodes from the trigger input of the pacer and, instead, couples decoded pulse trigger information that is transmitted from the external unit. Thus, in the EP mode, the pacing unit provides pacing pulses in a VVT mode synchronous with pulse trigger information signals transmitted from the external unit, instead of from the R-wave activity of the heart. The pacer itself operates in a conventional manner, responding to the externally-transmitted pulse signals in the same manner that it would respond to detected R-wave pulse signals.

The system of the present invention also transmits ECG information, in real time, to the external unit over a separate communication link. Thus, the system provides a two-way communication link whereby pacing pulse signals are received (preferably by radio frequency (RF) transmission) and ECG information is transmitted (preferably by an audio FM encoder) simultaneously, and in real time.

The external unit of the present invention employs a conventional programmable electrical stimulator, well-known to persons experienced in conducting EP studies. The stimulator receives ECG signals, as an input, and provides, as an output, pacing pulse signals in a conventional manner. The ECG input port of the stimulator is coupled with a receiver that detects and decodes the ECG information transmitted from the implanted unit. The pacing pulse output is provided, via a controller, to a transmitter which transmits the pacing pulse signals to the implanted unit. The controller also serves to effectuate mode change information.

The cardioverter/pacer unit of the present invention is preferably adapted to perform a full range of cardioverting (including defibrillating) functions in a fully automatic manner. Thus, the cardioverter/pacer unit not only performs EP studies, but automatically detects the onset of high-rate tachycardia and/or fibrillation and responds to such conditions by issuing appropriate cardioverting and/or defibrillating shocks. As such, if, during an EP study, the pacing pulses induce an arrhythmia condition, the unit will automatically respond to, and treat, the arrhythmia by delivering electrical shocks or impulses to the heart at a sufficient energy level and time to revert the heart to normalcy.

Thus, it is an object of the present invention to provide an implantable cardioverter/pacer unit, capable of providing cardioverting or pacing pulses to the heart of a patient in a conventional manner, but which can be converted to a system for conducting electrophysiology (EP) studies. In particular, it is an object of the present invention to provide an implantable unit for conducting EP studies using conventional implantable pacer technology whereby pacing pulse trigger information may be received, and ECG information may be transmitted, via a wireless communication path, to and from an external unit. The ECG signal information is transmitted from the implantable unit in real time. The use of such a system avoids the need for electrode wires extending through the skin of the patient, thus allowing EP studies to be conducted without further surgical implant.

Still further, it is an object of the present invention to provide an implantable unit for conducting EP studies that interfaces with a programmable pacer operable in a conventional manner, wherein the pacer can selectively receive trigger signals derived from the ECG activity of the heart, or from an external transmitter.

Still further, it is an object of the present invention to provide a system for conducting EP studies using a conventional programmable electrical stimulator as the interface with the operator of the system. The programmable stimulator is coupled with a transmitter and receiver for transmitting pulse information to the patient and for receiving ECG information from the patient. Accordingly, EP studies may be carried out in a conventional manner by operators already familiar with the conventional EP study techniques.

These and other objects of the invention will become apparent when reference is made to foregoing detailed description.

DETAILED DESCRIPTION OF A PREFERRED EMBODIMENT

Figure 1:
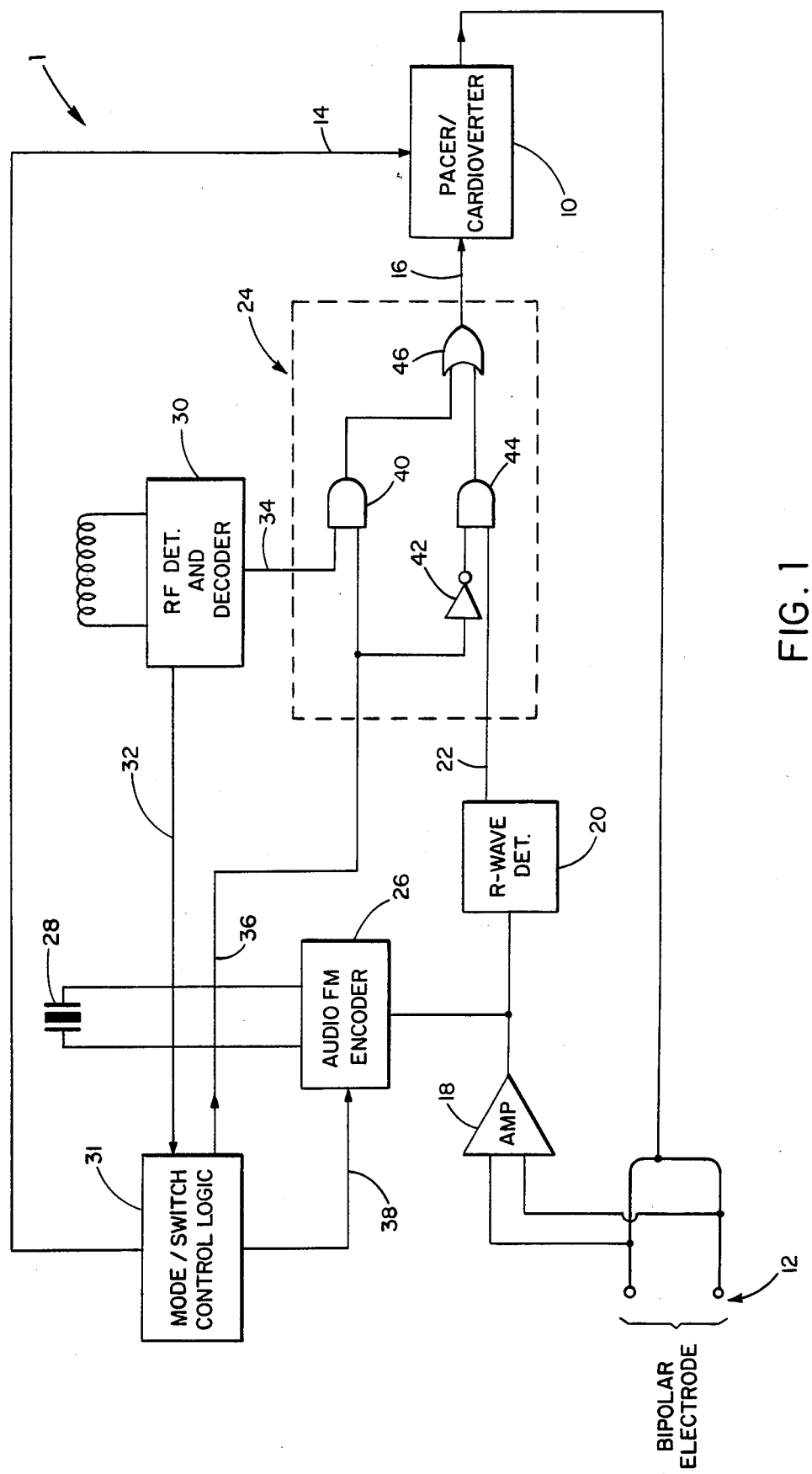
FIG. 1 is a schematic diagram of the implantable system for conducting EP studies.
Figure 2:
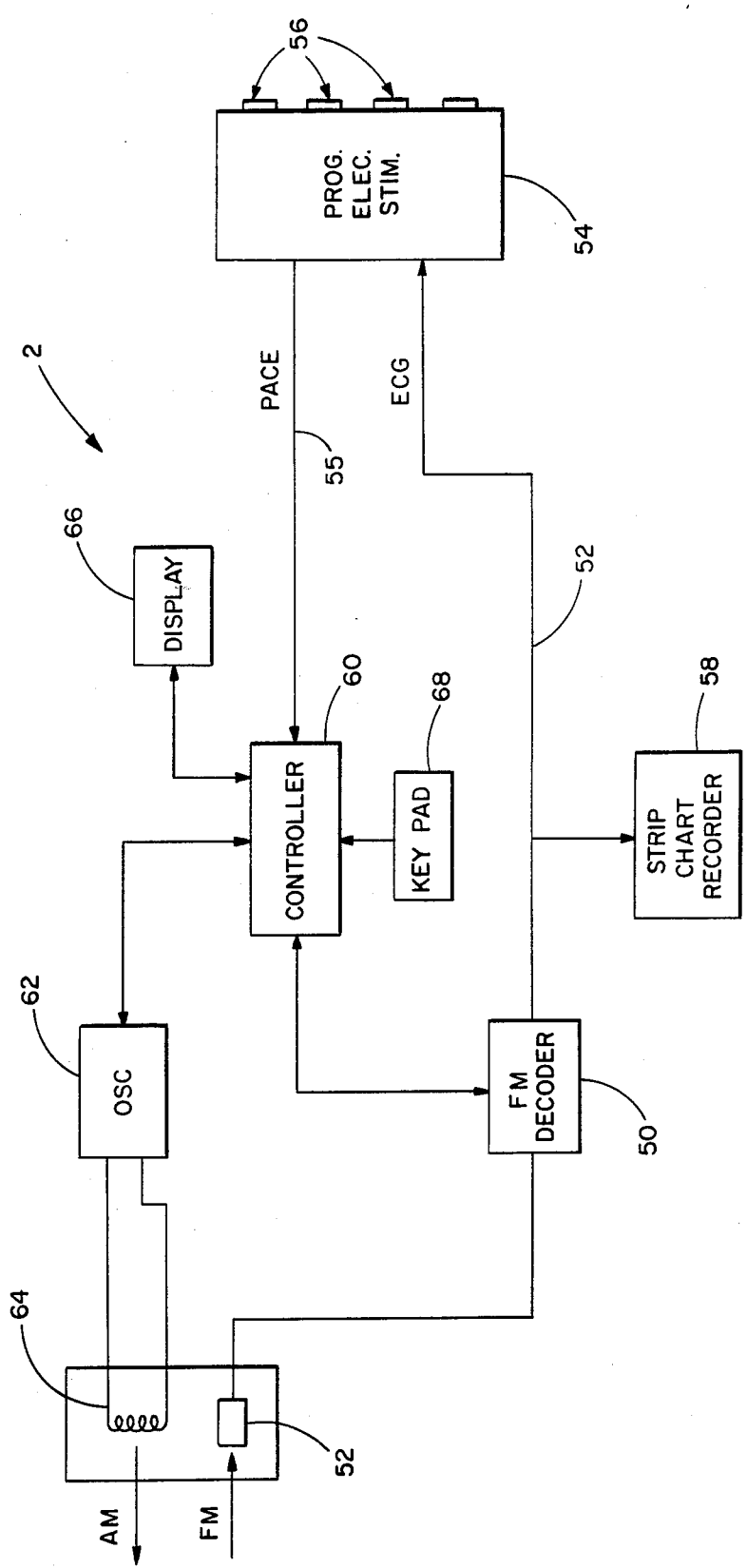
FIG. 2 is a schematic diagram of the external unit for conducting EP studies.

The apparatus of the present invention comprises an implantable cardioverter/pacer unit 1, as shown in FIG. 1, and an external unit 2, as shown in FIG. 2. The implantable unit 1 includes a programmable cardioverter/pacer 10 which delivers pacing pulses to the heart of a patient through bipolar electrodes 12. The bipolar electrodes 12 are in contact with the ventricle of the heart and serve to deliver pacing pulses in a conventional manner. The pacer 10 is preferably a multi-mode pacer, i.e. a pacer capable of operating in a number of conventional pacing modes such as the VOO, VVI, VVT, and Burst modes. Mode changes are effectuated by signals over line 14 provided to the pacer 10. It will be apparent that the pacer need not be operable in all of the above modes but, at a minimum in order to conduct EP studies in accordance with the present technique, the pacer must be capable of being placed in the VVT mode wherein the pacing output signals are synchronized with trigger signals provided to the trigger input of the pacer via line 16.

The cardioverter/pacer 10 is preferably capable of cardioverting, including defibrillating, in response to detection of an arrhythmia condition. Such cardioversion and defibrillation capabilities are well-known in the art. The unit 10 is thus coupled to defibrillator pulse delivery electrodes (not shown) that are associated with the heart of a patient for delivering a cardioverting or defibrillating shock to the heart. Thus, if, during an EP study, the heart goes into fibrillation, the unit 10 will automatically respond to such condition and deliver defibrillation shocks to the heart in a manner known in the art.

The bipolar electrodes 12 function to not only deliver pacing pulses to the ventricle of the patient's heart, but are also used to sense the ECG characteristics of the heart. The bipolar electrodes are connected to an amplifier 18 which amplifies the detected electrical activity of the heart. The amplified signals are provided to a conditioning circuit 20 which includes an R-wave detector. The conditioning circuit 20 provides a series of output pulses reflecting the series of R-waves generated by the heart beat activity. The R-wave signals are provided, over line 22, to a logical switch circuit 24 which performs in a manner to be described.

The amplified ECG signals from amplifier 18 are also provided to an audio FM transmitter or encoder 26. The audio FM transmitter 26 includes a piezoelectric transducer 28, preferably connected to the case of the implanted unit, which provides audio signals that are detectable externally of the patient. Transmission of ECG signals by FM techniques using a piezoelectric transducer is disclosed in co-pending U.S. patent application Ser. No. 502,499, filed on June 9, 1983, U.S. Pat. No. 4,567,883 and assigned to the same assignee as the instant application. As described therein, the analog ECG signals may be transmitted by FM using an audio oscillator. These transmitted signals are demodulated by an external receiver to recover the ECG signal. As set forth in the copending application, the ECG signal may be first converted to digital form and transmitted digitally using frequency shift keying techniques. It should be apparent to one of ordinary skill in the art that other techniques for transmitting the ECG information externally of the patient could be employed.

The implanted system 1 further includes a radio frequency detector and decoder 30 which receives both mode change information and pulse command signals from the external unit 2. The detector 30 is a conventional radio frequency detector and decoder. Upon receipt of a mode control signal, which may be in any digital code such as a 15 bit code, that indicates placement in the EP study mode, the RF detector 30 emits a logical high state signal over line 32 to control logic 31. The control logic 31, which may, in its simplest form, comprise an arrangement of logic gates, provides a mode control signal over line 14 to the pacer 10 to place the pacer in the VVT mode. Such mode control signal from the control logic may be a multi bit signal or may be a single bit signal in its most basic configuration. Following decoding of a signal to place the system in the EP study mode, the radio frequency detector and decoder 30 receives pulse command signals from the external unit 2. These pulse command signals are provided over decoder output line 34 to the logical switch 24.

When the control logic 31 receives a signal over line 32 indicative of the EP study mode, the control logic 31 emits a signal over line 14 to place the pacer 10 in the VVT mode and further provides a logical high, or one, signal over line 36 to the logical switch circuit 24. Still further, the control logic provides an enabling signal over line 38 to enable the audio FM encoder 26. The control logic 31 maintains this configuration until the radio frequency signals are no longer detected by the decoder 30 (thus resulting in a logical low, or zero, signal over line 32). Upon the absence of such radio frequency signals, the control logic output over line 36 reverts to a logical zero state. The logic signals over lines 14 and 38 may similarly be changed depending on the various mode selections that may be made, not pertinent to the present invention. That is, other modes may be employed whereby the control logic sets the pacer 10 in a VVI, VOO, or Burst mode. Similarly, such modes may also require that ECG information be transmitted, in which case the control logic provides an enabling signal over line 38 to the audio FM encoder 26. These various control logic signals and the various modes of operating the pacer, other than the EP mode, form no part of the present invention.

The logical switch 24 includes a series of logic gates to selectively couple the pulse command signals over line 34 or the R-wave pulse signals over line 22 to the trigger input of the pacer, via line 16. Such selection is determined by the state of the control line 36 from the control logic 31. That is, when the control line 36 is at a logical one state (i.e. when the system is in the EP study mode) the logical one signal is provided to an input of AND gate 40 and to inverter 42. The output of inverter 42 is coupled to an input of AND gate 44. The output of AND gates 40 and 44 are provided to OR gate 46, the output of which is provided over line 16 to a trigger input of the pacer 10.

Thus, if the system is in the EP study mode, such that the logic state of line 36 is high, pulse command signals detected by the RF receiver or decoder 30 are able to pass through the AND gate 40, through OR gate 46, and to line 16 to the trigger input of the pacer 10. In such mode, the output of inverter 42 is low thus preventing any R-wave signals over line 22 from passing through the AND gate 44. Thus, the pacer 10, placed in the VVT mode, emits pacing pulses to the bipolar electrodes in synchronism with the pulse command signals detected by the receiver 30.

If, on the other hand, the system is not in the EP mode, the control line 36 is at a logical zero state which makes the output of inverter 42 at a logical one state. Thus, R-wave signals detected by the R-wave detector 20 are provided over line 22, through AND gate 44, through OR gate 46, and over line 16 to the trigger input of the pacer 10. Pulse command signals from the receiver 30 are unable to pass through the AND gate 40. In such a condition, the pacer, in the VVT mode, provides pacing pulse signals to the bipolar electrodes in synchronism with the detected R-waves (or absence of R-waves). That is, the pacer operates in its conventional manner in the VVT mode.

The external unit 2, as shown in FIG. 2, includes a receiver comprising an FM decoder 50 coupled with a microphone 52 which detects the audio FM signals. The decoded FM signals, which are analog ECG signals, are provided over line 52 to the ECG input of a programmable electrical stimulator 54. The programmable electrical stimulator is a conventional device such as the Bloom Mode DTU101 or the Medtronic Model 2352. Such stimulators include various manual inputs, such as dials and switches 56, which are manipulated by the operator of the system to control the stimulating pacing pulses provided as an output over line 55. The decoded FM analog ECG signals are also provided to a strip chart recorder 56 in a conventional manner.

The pacing pulse signal output of the programmable electrical stimulator, over line 55, interfaces with a controller 60. The controller 60 may be a microprocessor-based unit that receives the pacing pulse signals and interfaces with a power oscillator 62 of a radio frequency amplitude modulated transmitter coil 64. The pacing pulse signals are converted to digital form by the controller 60 in a conventional manner and such digital signals are transmitted by the oscillator 62, via transmitter coil 64, to the internal unit 1 in a conventional manner. The controller 60 also interfaces with a display device 66 and a keypad 68. The keypad 68 is provided to input mode change information to the controller 60. The controller 60 also interfaces with the FM decoder 50 to receive the FM signal information, which may be desirable in certain operating modes.

In operation, when it is desired to conduct an EP study, the operator of the system, through the keypad 68, provides inputs to the controller 60 indicative of an EP mode. The controller then interfaces with the transmitter 62, 64, to transmit EP mode change signals to the internal unit 1. The radio frequency detector 30 within the internal unit decodes the signals and provides a control signal over line 32 to the control logic 31 which then places the implantable pacer 10 in the VVT mode over line 14. Further, the control logic 31 enables the audio FM encoder 26 for transmitting audio FM signals, in real time, to the external unit 2. Further, the control logic 31 provides a high signal over line 36 to the logic switch 24 to couple the decoder 30 output, over line 34, to the trigger input of the pacer 10 over line 16.

After the external unit 2 transmits the mode control information to the internal unit 1, the operator of the system then controls the programmable electrical stimulator 54 in a conventional manner to deliver pacing pulses to the heart of the patient as desired. The pacing pulse output of the programmable electrical stimulator, over line 55, is provided to the controller 60 and such pacing pulse signals are transmitted for detection by the receiver 30 of the implantable unit 1. The pacing pulse signals are decoded by the receiver 30 and the pulse signals are provided over line 34, via the logical switch 24, to the trigger input of the pacer 10. The pacer thus paces the heart in a VVT mode in accordance with the pacing pulse trigger signals selected by the operator. Simultaneously, ECG information is continuously transmitted from the implanted unit to the external FM receiver 50, 52 where it is converted to analog ECG signals and provided to the programmable stimulator 54.

Above, specific examples of the present invention have been described. It should be appreciated, however, that this description has been given for purposes of illustration only, and is in no way intended to limit the scope of the present invention. Rather, it is the intention that the present invention be limited only as defined in the appended claims.

What is claimed is:

1. A system for conducting electrophysiology studies using an implantable cardioverter/pacer comprising:
   an external electrical stimulator including means for receiving ECG data and means for providing pacer stimulating pulse data in accordance with control information manually provided by the operator of the system;
   an external transceiver including means for transmitting the pacer stimulating pulse data to an implantable pacer/control system, means for receiving ECG data from the implantable pacer/control system, and means for providing the ECG data to the external electrical stimulator;
   an implantable pacer/control system comprising;
   implantable electrode means for sensing ECG activity of the heart and for delivering pacing pulses to the heart;
   ECG transmitter means operatively connected with said implantable electrode means for transmitting ECG data, sensed by the electrode means, externally of the patient;
   receiving means for receiving and detecting the pacer stimulating pulse data and for providing pulse command signals in accordance with the detected pacer stimulating pulse data;
   R-wave detecting means coupled with said electrode means for detecting R-waves and for providing R-wave pulse signals corresponding to the detected R-waves;
   switching means for selectively coupling said receiving means and said R-wave detecting means with an implantable pacing means;
   control means for controlling said switching means to selectively couple one of said receiving means and R-wave detecting means with the implantable pacing means; and
   implantable pacing means for delivering pacing pulses to said implantable electrodes synchronous with either the pulse command signals of said receiving means or the R-wave pulse signals of said R-wave detecting means.

2. The system of claim 1 wherein said external transceiver further comprises means for transmitting an electrophysiology (EP) mode control signal to said receiving means of the implantable pacer/control system and wherein said receiving means includes means for decoding the EP mode control signal and for providing the decoded EP mode control signal to said control means and wherein said control means provides a switch control signal to said switching means, upon receipt of the decoded EP mode control signal, to couple said receiving means with said implantable pacing means.

3. The system of claim 2 wherein said control means provides a VVT control signal to said implantable pacing means, upon receipt of the decoded EP mode control signal, to place said implantable pacing means in a VVT mode.

4. The system of claim 2 wherein said control means provides a transmitter enabling signal to said ECG transmitter means to enable said ECG transmitter to transmit ECG data to said external transceiver means.

5. The system of claim 1 wherein said external transceiver comprises an RF transmitter for transmitting pacer stimulating pulse data and an audio FM decoder for receiving and decoding the ECG data.

6. The system of claim 5 wherein said ECG transmitter means comprises an audio FM transmitter for transmitting ECG data to said external audio FM decoder, said external audio FM decoder including an output coupled to said means for receiving ECG data.

7. The system of claim 1 wherein said ECG transmitter means includes means for transmitting ECG data as the ECG data is sensed by said implantable electrode means.

8. The system of claim 1 wherein said implantable pacing means includes a cardioverter/defibrillator means for detecting an arrhythmia condition and for automatically cardioverting and defibrillating the heart in response to the detection of an arrhythmia condition.

9. A control for an implantable multi-mode pacer for conducting electrophysiology (EP) studies, comprising:
   an R-wave detector including means for sensing the electrical activity of the heart, means for detecting the heart R-waves, and means for providing R-wave signals corresponding to the detected R-waves;
   pulse command means including means for receiving and providing externally generated pacing pulse command signals and externally generated mode control signals;
   implantable multi-mode pacing means for pacing the ventricle of a heart in at least the VVT mode and including a mode control input and a trigger input;
   switching means for selectively coupling the R-wave signals or the pulse command signals to the trigger input of said pacing means in accordance with a switch control signal from a control means;
   control means coupled with said pulse command means for providing a switch control signal to said switching means and a mode control signal to the mode control input of said pacing means, said switch control signal having a first state in absence of receipt of a mode control signal to couple the R-wave signals to said trigger input and a second state upon receipt of a mode control signal to couple the pulse command signals to said trigger input, said control means further comprising means for placing the pacing means in a VVT mode upon receipt of a mode control signal whereby the pacing pulse output of the pacing means is synchronized with said R-wave signals or said pulse command signals.

10. A system for conducting electrophysiology studies using an implantable pacer operable in the VVT mode comprising:
   an implantable unit including, a pacer operable in at least the VVT mode and having a trigger input;

R-wave detecting means for detecting heart R-waves; receiving means for receiving pulse command signals generated externally of the patient;

switching means for selectively connecting either the R-wave detecting means or the receiving means to said trigger input of said pacer;

control means for controlling the switching means in accordance with mode control signals generated externally of the patient; and an external unit including, transmission means for transmitting pulse command signals and mode control signals to the implantable unit.

* * * * *